United States Patent [19]
Langlois

[11] 3,964,052
[45] June 15, 1976

[54] ACOUSTICAL IMAGING SYSTEM
[75] Inventor: Gary Norris Langlois, Richland, Wash.
[73] Assignee: Holosonics, Inc., Richland, Wash.
[22] Filed: Mar. 28, 1975
[21] Appl. No.: 563,219

[52] U.S. Cl. .............................. 340/5 H; 73/67.5 H
[51] Int. Cl.² ........................................ G01N 29/04
[58] Field of Search ...................... 340/5 H, 5 MP; 73/67.5 R, 67.5 H

[56] References Cited
UNITED STATES PATENTS
3,832,888  9/1974  Langlois ........................... 73/67.5 H Primary Examiner—Richard A. Farley
Attorney, Agent, or Firm—Woodcock Washburn Kurtz & Mackiewicz

[57] ABSTRACT
An improved system for ensonifying an object, which comprises upper and lower fluid-filled chambers. The chambers are separated by a partition including a lens; a further, movable lens may be disposed within the upper chamber. A reflective-type detector is disposed in the floor of the bottom chamber, and ports provided at opposite sides of the chamber for light impinging upon, and reflected from, the detector surface. A resilient closure at the upper end of the upper chamber conformably receives the surface of an object to be ensonified. A transducer producing the object, or ensonifying, acoustic beam is disposed within another fluid-filled enclosure one wall of which comprises a flexible membrane. The latter membrane is disposed against the upper side of the object to be ensonified and conforms thereto so that a relatively continuous fluid path is presented between the transducer and the object, and from the object to the detector.

In a preferred embodiment, a reference acoustic beam is produced by another transducer disposed within the lower chamber, the angle between the object and reference beams which impinge upon the detector advantageously being at least 60° to 75°.

19 Claims, 2 Drawing Figures

ACOUSTICAL IMAGING SYSTEM

BACKGROUND OF THE INVENTION

The present invention relates to the field of acoustical holography and, more particularly, to an improved system for effecting acoustical imaging.

Acoustical holography, which involves the generation of holograms through the production of interfering patterns of acoustical waveforms, has been known for some time. One early example of an apparatus for practicing acoustical holograph is disclosed in U.S. patent application Ser. No. 569,914 - Brenden, filed Aug. 3, 1966 and entitled "Ultrasonic Holography", now U.S. Pat. 3,879,989. In this patent means are shown for producing a pattern of perturbations at the interface of two fluids in response to the impingement of a pair of ultrasonic beams. The wave trains of each beam give rise to irregularities upon the liquid interface, the pattern of perturbations representing the phase relationships between various portions of the beams. By using one unmodulated beam as a reference, the pattern resulting from interference between it and a beam whose wavefront phase is spatially modulated will represent the characteristics of the modulation of the second beam.

Modulation of an acoustical beam may, for example, result from the presence of an object of varying acoustical transparency in the path of the beam. The interference pattern will the represent variations in the acoustical transmissivity of the object. In this manner a representation can be produced of the inner structure of an optically opaque object, such as flaws or voids within a metal casting or the arrangement of tissue within the human body.

In order to record or display the interference pattern given rise to by the reference and the object beams, it is known to illuminate the pattern with a beam of visible light. The light which is reflected from the pattern, hereinafter referred to as a hologram, is then directed to appropriate apparatus for recording or displaying the hologram.

While the science of acoustical holography has made substantial progress in recent years, many problems still exist in satisfactorily implementing the technique.

With one prior art approach, for example, a reference and an object beam are directed from beneath upon a detection device disposed in an acoustically transmissive liquid. An illuminating beam of light is directed upon the top of the detector. In such an arrangement, however, multiple reflections of acoustical energy within the detector structure degrade the quality of the hologram.

The detectors to be used with imaging systems have themselves also presented substantial problems. In particular, many of the detectors heretofore known have been relatively inefficient, i.e., much of the acoustic and/or optical energy directed toward the detector was lost as the result of inefficient or unwanted reflection or due to absorption.

In addition most prior art imaging systems rely upon mirrors to deflect either the reference or the object beam or both so that ensonification, production of a hologram, and imaging might be accomplished at convenient locations.

It is therefore an object of the present invention to provide an improved acoustical imaging system.

It is a further object of the invention to provide a compact system for producing a hologram from acoustic signals.

Still another object is to provide an improved acoustical holography imaging system for use with a liquid metal area detector.

SUMMARY OF THE INVENTION

Briefly stated, in accordance with one aspect of the invention the foregoing objects are achieved by providing a lower liquid-filled enclosure having therein a detector which comprises a thin layer of liquid metal disposed over a rigid substrate. Optically transparent windows are formed in the sides of the enclosure to allow illuminating radiation to impinge upon the detection surface and be reflected therefrom to appropriate utilization means.

An acoustic transducer is mounted in an uppermost enclosure filled with fluid and having a flexible wall in order to conform to the contours of an object under inspection. Also disposed above the lower enclosure is a closure formed by a fluid-filled envelope which conformably receives the object under inspection and provides a path for an object acoustic beam.

In one preferred embodiment the lower enclosure is divided into upper and lower portions by means of a partition including an acoustic lens. A second lens is adjustably mounted within the upper portion to aid in focusing the object beam upon the detector surface.

BRIEF DESCRIPTION OF THE DRAWING

While the specification concludes with claims particularly pointing out and distinctly claiming the subject matter which is regarded as the invention, it is believed that the invention will be better understood from the following description of a preferred embodiment taken in conjunction with the accompanying drawing in which:

DESCRIPTION OF A PREFERRED EMBODIMENT

Figure 1:
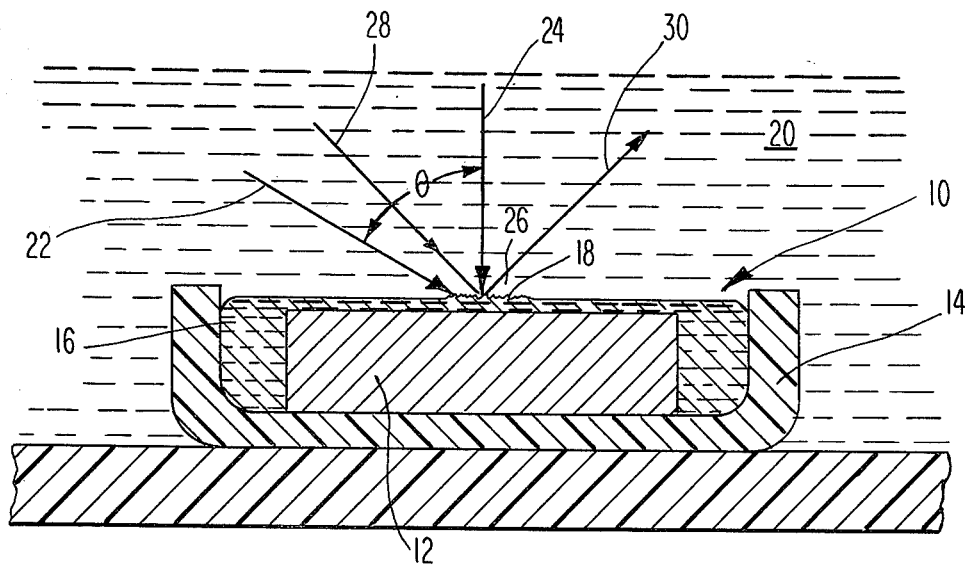
FIG. 1 is a cross-sectional diagram of a detector suitable for use with the present invention.

Turning now to FIG. 1, there is shown an improved detector which is well adapted for use with the present invention and which obviates many of the problems experienced with prior art detection devices. The detector, which also forms the subject matter of copending U.S. application Ser. No. 563,126 filed Mar. 18, 1975, is generally indicated at 10 and comprises a rigid substrate 12 which in a successfully tested embodiment was constituted by a brass plate having a thickness of approximately 2.5 cm. The substrate is disposed within an enclosure 14, and a liquid metal 16 added to the enclosure in sufficient quantity to form a thin layer over the upper surface of substrate 12.

In one successfully tested embodiment the layer of liquid metal overlying the brass substrate was adjusted to a depth of approximately 1 mm. While this dimension is not critical and may be varied to suit a given application, should the layer be unnecessarily thick it may become susceptible to disturbance by extraneous vibrations. On the other hand, if the layer is too thin it will not deform to the degree necessary to form a satisfactory hologram.

In a preferred embodiment, the liquid metal 16 is mercury. If mercury is used, it is important that enclosure 14 be of a material such as glass or plastic which does not exhibit an affinity for the mercury. By this is meant that the material of enclosure 14 is not one over whose surface the mercury will migrate.

In order to form an appropriate surface 18 for the production of a holographic image, it is highly desirable that the upper surface of substrate 12 be flat and smooth. In practice it has been found that good results are achieved by maintaining the surface of the substrate flat within a tolerance of ⅛ of the shortest acoustic wavelength to be utilized. Further, in order to support a relatively thin layer of liquid metal the substrate surface must be of a material which will be wetted by the liquid metal. When the liquid metal used is mercury, a brass surface has been found to provide the requisite wetting characteristic. Further, by using a brass substrate an additional benefit accrues in that the brass-mercury interface exhibits a low reflection coefficient for acoustic energy so that most of the acoustic energy which penetrates the layer of mercury is absorbed by the brass substrate.

To prevent spurious vibrations from arising in the substrate it is advisable that it be securely fastened to a rigid foundation, or that it be of substantial thickness. Experimental use has shown that a brass substrate having a thickness of approximately 2.5 cm is adequate for most purposes.

In use, detector 10 is immersed in a body of transmissive fluid 20 which may, for instance, be water. In actual use, it has been found that the interface between the mercury 16 and water becomes somewhat cloudy, particularly when the pH of the water is 7 or greater. Although the mercury still exhibits a substantially higher degree of reflectivity than interfaces between many materials used in prior art detectors, the reflectivity of the mercury surface can be still further improved by maintaining the pH of the transmissive fluid in the range of approximately 5 to 6. This can easily be achieved by adding an appropriate amount of hydrochloric acid to water. With a bright surface on the mercury it reflects approximately 75% of incident visible light, as compared with approximately 1.4% for a fluorinated ether-air interface.

In order to create the perturbations in the surface 18 of the liquid metal which constitute a hologram, a pair of acoustic beams 22 and 24 are directed thereon. In the illustrated embodiment, beam 24 represents an acoustic object beam, the phase of whose wavefronts have been modulated as the result of their passage through an object to be examined. Beam 22 represents a reference acoustic beam which is of the same frequency, and substantially in phase with beam 24. In a preferred mode of construction the object beam 224 is oriented normal to the surface 18 of liquid metal 16, while reference beam 22 is inclined at a relatively large angle $\theta$ with respect to beam 24. In one successfully tested embodiment, an angle $\theta$ of substantially 60°–75° was found satisfactory.

In order to optically reproduce the hologram 26 which is given rise to by interfering wavefronts of the acoustic beams, a light beam 28 is directed obliquely upon surface 18. The beam is then reflected and refracted from the hologram 26, the resulting light 30 then comprising an image of the hologram which may be displayed upon a screen or recorded by suitable means for display at a subsequent time.

While in a presently preferred embodiment a brass substrate is utilized in conjunction with mercury, it will be recognized by those skilled in the art that other materials may alternatively be selected. For example, another example of a liquid metal-substrate combination which lends itself to use in the detector shown in FIG. 1 is liquefied gallium distributed over a glass substrate. It is known that gallium wets a glass surface and that liquid gallium provides a reflective surface. Further, gallium is not susceptible to evaporation and/or diffusion losses such as are experienced with some prior art detectors and may therefore be used in air. On the other hand, it is thought that a layer of gallium may be less sensitive to impingent acoustic signals than will mercury.

It will, of course, be seen that other liquefied metals such as cesium or rubidium may be selected for use, and that many materials other than the examples recited herein are well suited for use as substrates. In addition, the use of enclosure 14 is exemplary only, it being apparent that means for constraining liquid metal 16 might be formed integrally with the bottom of the enclosure which contains transmissive liquid 20; or the substrate should be placed directly over the floor of the enclosure, and the upstanding sidewalls of the enclosure used to confine the liquid metal. Still other variations of the inventive detector disclosed herein may additionally be thought of, it being recognized that the particular construction disclosed herein represents only the best mode currently known to the inventor.

Figure 2:
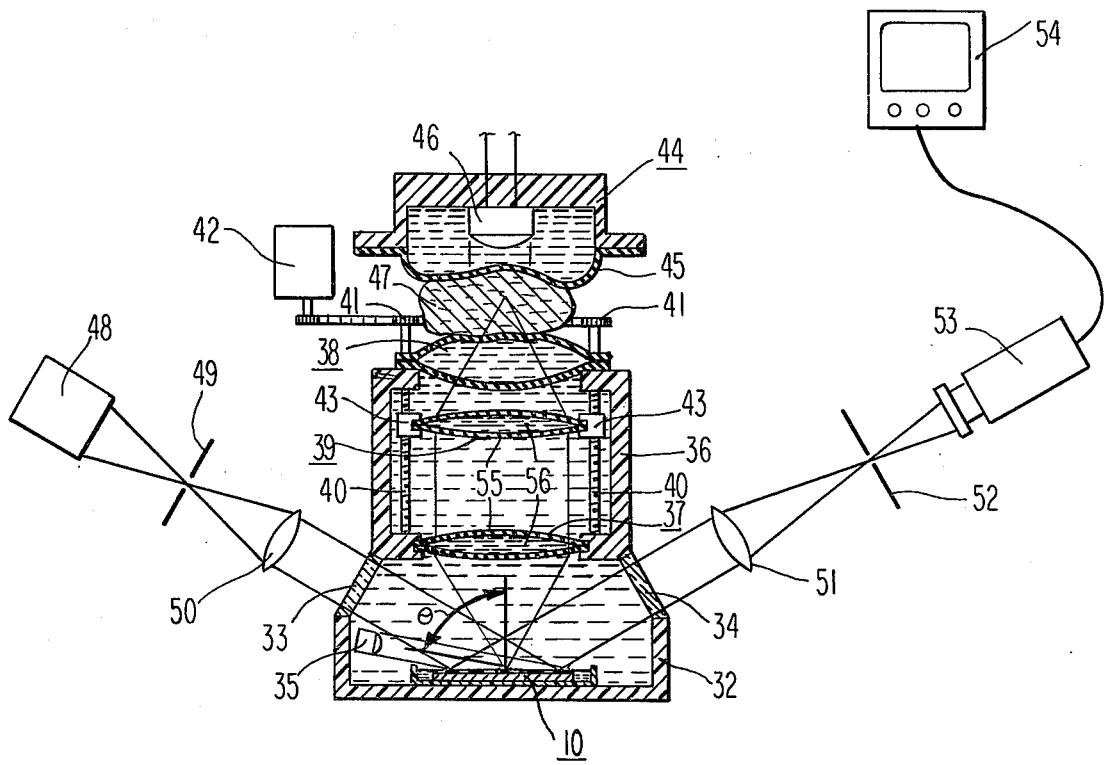
FIG. 2 is an elevational view in partial cross-section of an improved imaging system incorporating the detector of FIG. 1 and constructed in accordance with the teachings of the present invention.

FIG. 2 shows the acoustical imaging system which forms the subject matter of the present invention and depicts one implementation of the detector which was illustrated at FIG. 1. The detector 10 is disposed at the bottom of a fluid-filled enclosure. In the lateral walls of the enclosure, and at approximately opposite sides thereof, are disposed a pair of optically transmissive windows 33 and 34. An acoustic transducer 35, which may for instance be of piezoelectric type, is mounted within the enclosure and directed at an oblique angle to the liquid metal surface of detector 10.

In a presently preferred embodiment the fluid-filled enclosure comprises an upper chamber 36 disposed above a lower chamber 32. The chambers are separated by a partition which advantageously includes an acoustic lens 37. The upper end of chamber 36 is sealed by means of a liquid-filled closure 38. Closure 38 advantageously comprises an envelope made of natural rubber or the like which is filled with a quantity of water. Natural rubber is a preferred material for the closure as, among the commonly available materials, it is the least absorptive of acoustic energy. In addition, natural rubber produces only minimal reflection of an impingent acoustic signal.

Disposed within the upper chamber 36 is a second acoustic lens 39 which cooperates with lens 37 to focus an acoustic object beam upon detector 10. Various types of acoustic lenses are known, for instance as shown in U.S. Pat. No. 3,765,403 – Brenden. In a preferred embodiment, an envelope 55 of polystyrene may be used for the outer surfaces of the lenses. The envelope 55 is filled with a liquid 56 which may advantageously be Freon 113, "Freon" being a trademark used by the E. I. du Pont de Nemours Corporation to designate a particular type of fluorinated hydrocarbon.

Also disposed within upper chamber 36 are a plurality of lead screws 40 which extend vertically through the enclosure, the upper ends of the screws being linked by means of sprockets 41 to a chain so that they may be rotated in synchronism by means of suitable driving means such as electric motor 42. Followers 43, which may comprise recirculating ball nuts, are threadedly engaged by the lead screws and are affixed to a frame carrying movable lens 39. In this manner lens 39 may be moved to an appropriate vertical position in order to focus the acoustic object beam upon the surface of detector 10.

Disposed above the water-filled closure 38 is still another enclosure generally designated 44, one wall of which comprises a flexible membrane 45 and which is filled with a suitable sound-transmissive liquid such as water. Also disposed within enclosure 44 is a transducer 46 which produces a beam of acoustic energy. The latter beam, referred to as the object beam, is directed through the membrane 45 to an object 47 to be inspected. It will be recognized by those skilled in the art that the use of flexible membranes for contacting an object to be inspected allows the transmissive fluid to be brought into close proximity with the object, so that any discontinuities in the path of an impingent acoustic beam will be those within the object. In other words, it is desirable that spatial modulation of the object beam occur only in response to characteristics of the object under inspection, and not because of any other discontinuities, voids, or other variations in the path of the beam.

The upper surface of detector 10 is illuminated by electromagnetic energy from source 48. While the energy will be referred to as "light" and treated as visible light for purposes of description, it is readily apparent to those skilled in the art that infrared and ultraviolet energy, as well as monochromatic light, may be used and are therefore regarded as being encompassed by the term light as used herein. Thus it will be understood that other forms of electromagnetic radiation outside the visible portion of the spectrum may be selected for a particular adaptation of the present invention.

In the embodiment shown, an opaque element 49 having a small aperture or "pinhole" therein is utilized in conjunction with source 48 to provide an effective point source of light. In this manner, light is provided which is at least partially coherent. It may alternatively be desired to use totally coherent light, in which case a laser may be provided. One such device which is believed to be particularly adaptable for use with the disclosed invention is a laser of the pulsed argon ion type. The light produced by the source is directed upon a suitable lens 50, and passes through window 33 to impinge upon the surface of detector 10 at an oblique angle.

Acoustic transducer 35 is also oriented so as to direct a beam of acoustic energy toward the surface of the detector. In a preferred embodiment, the angle $\theta$ formed between the object beam and the reference beam is in the range of approximately 60°–75° so that the reference acoustic beam is directed obliquely to the detector surface. The inventor has found that as the angle $\theta$ increases, increasing amounts of energy can be supplied by the reference beam without disrupting the hologram. This is important since a higher-energy reference beam produces commensurately better sensitivity at the detector surface, and in particular can be used to achieve good resolution in the presence of an object beam of very low energy. In this manner a lack of energy in the object beam may be compensated for by an increase in energy of the reference beam, assuming that the angle $\theta$ between the object and reference beams is sufficiently large. By using a sufficiently large angle $\theta$, and a sufficiently energetic reference beam, the amount of acoustic energy necessary to properly ensonify the object 47 under inspection can be minimized. By reducing the amount of energy required for ensonifying the object, the likelihood of injury to living tissue is reduced and the utility of the system in examining living organisms is enhanced.

Light reflected from the surface of detector 10, with the hologram formed thereon by the interfering acoustic beams, escapes from lower enclosure 32 through window 34 and is collimated by means of lens 51. The light reflected from the surface of detector 10 contains a number of diffracted beams, as set forth in U.S. Pat. Nos. 3,564,904 and 3,564,905 — Brenden et al. and U.S. Pat. Nos. 3,585,847 and 3,765,403 — Brenden. These diffracted beams are focused at different points by lens 51. A spatial filter which, for instance, may comprise a thin plate 52 having a pinhole aperture about 400 microns in diameter, selectively transmits the desired component of the reflected light to appropriate means for recording and/or displaying the hologram. In the illustrated embodiment, a video camera 53 is shown coupled to a television receiver 54 so that the image formed from the hologram produced at the surface of detector 10 may be viewed immediately upon production.

In operation, transducers 35 and 46 are energized so that acoustic energy from transducer 46 ensonifies object 47. The varying density of object 47 spatially modulates the object beam in phase and amplitude. The object beam then passes through closure 38 and the fluid-filled enclosure and impinges upon the surface of detector 10. At the same time a reference acoustic signal from transducer 35 is directed upon detector 10, forming an angle $\theta$ with the object beam. The interfering acoustic wavefronts then give rise to a hologram at the surface of the detector which is illuminated by light source 48 and ultimately displayed upon the screen of television receiver 54.

As is set forth in the above-noted U.S. Pat. No. 3,765,403 to minimize adverse effects due to a light source of finite size, imperfections in the transmitting and detector fluids and other degradation factors, it is desirable to focus the viewing optics of the imaging system on a plane as close as possible to the hologram surface. Some loss in image resolution is encountered, however, and in order to improve the resolution acoustic lenses may be used to place the focused image at the hologram surface.

In the illustrated embodiment stationary lens 37 and movable lens 39 perform this function, lens 37 also serving as part of a partition dividing the enclosure into upper and lower chambers. In order to focus the object beam produced by transducer 46 motor 42 is operated to raise or lower lens 39 to an appropriate position. Lens 39, in conjunction with lens 37, focuses the acoustic energy penetrating object 47 upon the surface of detector 10. At the same time, a reference beam of acoustic energy from transducer 35 is caused to impinge upon the surface of the detector at an angle $\theta$ with respect to the object beam.

In a preferred embodiment transducers 46 and 35 are excited by means of radio frequency signals to produce wave trains at a frequency in the range of 0.5 to 15 MHz. It has been found advantageous to pulse or repeat wave trains in the indicated frequency range at a frequency below approximately 1 KHz, the wave trains of each pulse persisting for a period of approximately 100 microseconds. Of course, it is desirable that the wave trains produced by transducers 46 and 35 be of the same frequency so as to produce a meaningful interference pattern upon the surface of the detector of the system.

Due to the disposition of detector 10 at the bottom surface of the first enclosure 32 it is relatively immune from vibration, when compared to the immersed detectors found in the prior art. However, it will be seen that by providing two separate fluid chambers the integrity of the lower chamber can be maintained despite the introduction of dirt, impurities, etc. into the upper enclosure. The latter problem is particularly acute where an operating mechanism, such as the lens positioning apparatus shown in FIG. 2, is present within the upper enclosure. It will be appreciated by those skilled in the art that if impurities are introduced into the transmissive fluid in the lower chamber they may attack or react with the liquid metal used in the detector. For this reason it is especially important to maintain the purity of the fluid in the lower chamber. Still further, it may be found desirable to use different fluids in the first and second chambers. For instance, should mercury be used as the liquid metal in detector 10, it will be desirable to use an aqueous hydrochloric acid solution in the lower enclosure which has a pH in the range of from 5 to 6. The solution, however, may have a detrimental effect upon the mechanism in the upper enclosure, or may alternatively necessitate the use of materials which are expensive and/or difficult to work with in the fabrication of the mechanism. Aside from this, there may be still other reasons necessitating the use of two different fluids in the first and the second enclosures. In any of these cases, the use of separate but juxtaposed fluid enclosures is a highly desirable attribute of the illustrated apparatus.

Another advantage of the illustrated acoustic imaging system is the fact that it makes it unnecessary to place a detector above an object to be ensonified. In addition, with the vertical orientation of the object beam transducer, the object to be ensonified, the various lenses, and the detector it is unnecessary to provide the system with complex and expensive reflecting elements to orient the acoustic and/or electromagnetic beams in a useful configuration.

As will be evident from the foregoing description, certain aspects of the invention are not limited to the particular details of the examples illustrated, and it is therefore contemplated that other modifications or applications will occur to those skilled in the art. It is accordingly intended that the appended claims shall cover all such modifications and applications as do not depart from the true spirit and scope of the invention.

What is claimed as new and desired to be secured by Letters Patent of the United States is:

1. An acoustical imaging system comprising:
   a first enclosure for confining a liquid therein and having an opening in an upper surface thereof;
   a detector disposed beneath said opening and within said first enclosure and having a surface exhibiting a pattern of deformations when impinged upon by acoustic energy;
   a first source of acoustic energy adapted to direct a first beam of said energy upon said detector surface at an oblique angle thereto;
   a first yieldable acoustically transparent member closing said opening in said first enclosure for coupling the interior of said first enclosure to an object to be examined;
   a second enclosure for confining a liquid therein and including a second yieldable acoustically transparent portion for coupling the interior of said second enclosure to the object;
   a second source of acoustic energy disposed within said second enclosure and adapted to direct a second beam of said energy through the object toward and substantially normal to said detector surface;
   means for directing illuminating radiation upon the surface of said detector; and
   means for observing said surface.

2. An acoustical imaging system according to claim 1, wherein said detector is disposed upon a lower horizontal surface of said first enclosure.

3. An acoustical imaging system according to claim 2, wherein said first yieldable acoustically transparent member comprises a flexible envelope filled with liquid.

4. An acoustical imaging system according to claim 3, further including first and second optically transparent members disposed at opposite sides of said first enclosure for allowing illuminating radiation to be directed upon and reflected from said detector.

5. An acoustical imaging system according to claim 4, further including partition means dividing said first enclosure into a first, lower and a second, upper chamber, said partition means comprising a first acoustic lens;
   a second acoustic lens adjustably disposed in said second, upper chamber intermediate said yieldable acoustically transparent member and said first acoustic lens; and
   means for adjustably positioning said second acoustic lens with respect to said first acoustic lens.

6. An acoustical imaging system comprising:
   a first enclosure having a liquid disposed therein;
   a detector submersed in said liquid;
   partition means dividing said enclosure into first and second chambers, said second chamber being above said first chamber, said partition means including an acoustically transparent portion;
   said first enclosure having an opening in the upper surface thereof above said acoustically transparent portion;
   a flexible liquid-filled closure for closing said opening and for conformably receiving an object to be examined;
   a first source of acoustic energy disposed in said first enclosure for directing a first beam of acoustic energy upon said detector at an angle $\theta$ with respect to a normal to a surface thereof;
   a second source of acoustic energy adapted to be disposed at the opposite side of said object from said closure for directing a second beam of acoustic energy through said object and said enclosure to said detector, said beam impinging upon said detector in a direction substantially normal thereto; and
   means for observing a deformation pattern produced upon said detector by said acoustic energy beams.

7. An acoustical imaging system according to claim 6 wherein said acoustically transparent portion comprises a first acoustic lens; and further including a second acoustic lens disposed within said second chamber and adapted to be adjustably positioned between said first acoustic lens and said closure.

8. An acoustical imaging system according to claim 7, further including optical window means disposed at substantially opposite sides of said first chamber for allowing illuminating radiation to be directed upon and reflected from said detector.

9. An acoustical imaging system according to claim 6, wherein said detector comprises a substantially rigid substrate having disposed thereon a relatively thin layer of liquid metal.

10. An acoustical imaging system according to claim 9, wherein said liquid metal is mercury.

11. An acoustical imaging system according to claim 10, wherein the liquid in said first enclosure is an aqueous acid solution having a pH in the range of from 5 to 6.

12. An acoustical imaging system according to claim 11, further including a light source for directing light through said window means upon said detector surface; and means for receiving the light reflected from said surface.

13. An acoustical imaging system comprising:
a first enclosure for confining an acoustically transmissive liquid therein;
a detector disposed upon a lower surface within said enclosure, said detector including a substantially rigid substrate, a volume of liquid metal disposed over an upper surface of said substrate, and means for retaining said liquid metal upon said substrate;
acoustically transparent, flexible means disposed at the uppermost surface of said enclosure for conformably receiving an object to be ensonified;
a first source of acoustic energy for directing a first beam of said energy upon the surface of said liquid metal;
a second enclosure for confining an acoustically transmissive liquid therein and including a flexible wall portion for conformably adjusting to the surface of the object;
a second source of acoustic energy disposed within said second enclosure for directing a second beam of said energy through an object to be ensonified and to said liquid metal surface;
means for directing electromagnetic radiation upon said liquid metal surface for illuminating said surface; and
means for observing the illuminated surface.

14. An acoustical imaging system according to claim 13, wherein said liquid metal is mercury and said substrate is formed of a material wettable by mercury.

15. An acoustical imaging system according to claim 14, wherein the acoustically transmissive liquid comprises an aqueous solution of hydrochloric acid having a pH in the range of from 5 to 6.

16. An acoustical imaging system according to claim 15, further including first and second optically transparent members disposed in opposite sides of said first enclosure for allowing said radiation to be directed upon and reflected from the surface of said liquid metal.

17. An acoustical imaging system according to claim 16, further including acoustic lens means disposed within said first enclosure; and means for adjustably positioning said lens means intermediate said closure and said detector.

18. An acoustical imaging system according to claim 17, further including partition means dividing said first enclosure into first and second chambers, at least a portion of said partition means comprising a second acoustic lens.

19. An acoustical imaging system according to claim 18, wherein said acoustic lenses comprise acoustically transparent membranes confining fluid therebetween.

* * * * *

UNITED STATES PATENT OFFICE
CERTIFICATE OF CORRECTION

Patent No. 3,964,052          Dated June 15, 1976

Inventor(s) Gary Norris Langlois

It is certified that error appears in the above-identified patent and that said Letters Patent are hereby corrected as shown below:

Col. 1, line 12: change "holograph" to --holography--;

Col. 2, line 52: change "No. 563,126" to --No. 563,123--.

Col. 3, line 55: change "224" to --24--.

Col. 7, line 12: change "However" to --Moreover-- .

Signed and Sealed this

Fifth Day of October 1976

[SEAL]

*Attest:*

RUTH C. MASON  
*Attesting Officer*

C. MARSHALL DANN  
*Commissioner of Patents and Trademarks*